(12) United States Patent
Plumb et al.

(10) Patent No.: US 7,938,961 B2
(45) Date of Patent: *May 10, 2011

(54) CAPILLARY LOOP WITH A BUILT-IN RETAINING FRIT

(75) Inventors: Robert S. Plumb, Milford, MA (US); Chris L. Stumpf, Uxbridge, MA (US); Jennifer H. Granger, Northborough, MA (US)

(73) Assignee: Waters Technologies Corporation, Milford, MA (US)

( * ) Notice: Subject to any disclaimer, the term of this patent is extended or adjusted under 35 U.S.C. 154(b) by 1145 days.

This patent is subject to a terminal disclaimer.

(21) Appl. No.: 11/195,232

(22) Filed: Aug. 2, 2005

(65) Prior Publication Data

US 2006/0016755 A1 Jan. 26, 2006

Related U.S. Application Data

(63) Continuation of application No. PCT/US2004/002967, filed on Feb. 3, 2004.

(60) Provisional application No. 60/444,749, filed on Feb. 4, 2003.

(51) Int. Cl.
*B01D 15/08* (2006.01)
(52) U.S. Cl. ..................... 210/198.2; 210/656
(58) Field of Classification Search ............. 210/198.2, 210/635, 656; 422/70
See application file for complete search history.

(56) References Cited

U.S. PATENT DOCUMENTS

| | | | |
|---|---|---|---|
| 3,398,512 A * | 8/1968 | Perkins, Jr. et al. ............. 96/107 |
| 3,682,315 A | 8/1972 | Haller | |
| 3,692,669 A * | 9/1972 | Bauman ........................ 210/656 |
| 4,283,280 A | 8/1981 | Brownlee | |
| 4,350,595 A * | 9/1982 | Gunkel ........................... 21/656 |
| 4,469,597 A * | 9/1984 | Mott .............................. 21/198.2 |
| 4,587,014 A * | 5/1986 | America ..................... 210/198.2 |
| 4,676,898 A * | 6/1987 | Saxena ....................... 210/198.2 |
| 4,708,782 A * | 11/1987 | Andresen et al. .......... 210/198.2 |
| 4,740,298 A * | 4/1988 | Andresen et al. .......... 210/198.3 |
| 4,792,396 A | 12/1988 | Gundelfinger | |
| 4,882,047 A * | 11/1989 | Shalon ....................... 210/198.2 |
| 4,968,421 A | 11/1990 | Spacek et al. | |
| 5,013,433 A * | 5/1991 | Shalon ....................... 210/198.2 |
| 5,188,730 A | 2/1993 | Kronwald | |
| 5,238,556 A * | 8/1993 | Shirkhan ................... 210/198.2 |
| 5,246,577 A | 9/1993 | Fuchs | |
| 5,863,428 A * | 1/1999 | Ma et al. .................... 210/198.2 |
| 6,132,605 A | 10/2000 | Leavesley et al. | |
| 6,174,406 B1 * | 1/2001 | Gaynes et al. ................ 156/295 |
| 6,177,008 B1 * | 1/2001 | Treiber et al. ............. 210/198.2 |
| 6,224,775 B1 | 5/2001 | Foley et al. | |

(Continued)

FOREIGN PATENT DOCUMENTS

WO WO 00/10675 * 3/2000

*Primary Examiner* — Ernest G Therkorn
(74) *Attorney, Agent, or Firm* — Anthony J. Janiuk; Siqun Huang

(57) ABSTRACT

Disclosed herein are an apparatus and method for effectuating increased chromatographic efficiency in a capillary column by employing a retaining frit disposed within an analytical capillary. By disposing the retaining frit within the analytic capillary, the void volume is significantly minimized. The columns and methods described herein produce a simplified analytical capillary and retaining frit apparatus that provides greater chromatographic efficiency. Additionally, the column of the instant invention maintains chromatographic fidelity by reducing the transfer diameter as well as facilitating fluidic connections in situ.

14 Claims, 7 Drawing Sheets

U.S. PATENT DOCUMENTS

| | | | |
|---|---|---|---|
| 6,365,050 B1 * | 4/2002 | Cauchon | 21/635 |
| 6,527,951 B1 * | 3/2003 | Tuvim | 210/198.2 |
| 2003/0021730 A1 | 1/2003 | Muller | |
| 2005/0077175 A1 * | 4/2005 | Eisenbeiss et al. | 204/400 |
| 2006/0144770 A1 * | 7/2006 | Granger et al. | 210/198.2 |
| 2006/0186029 A1 * | 8/2006 | Granger et al. | 210/198.2 |

* cited by examiner

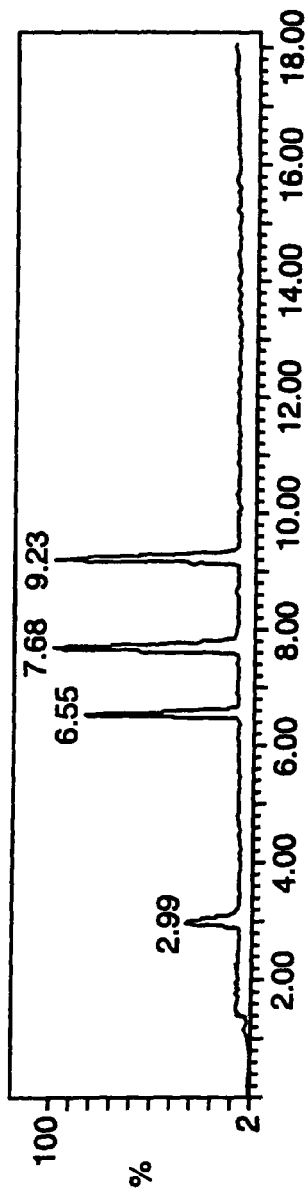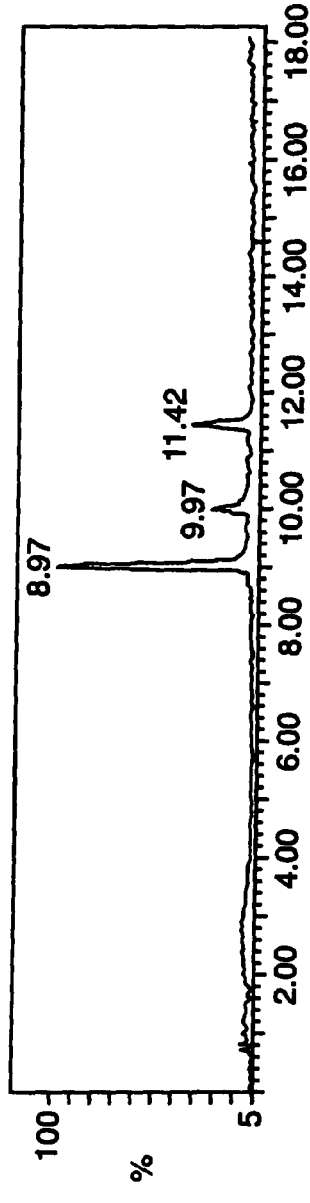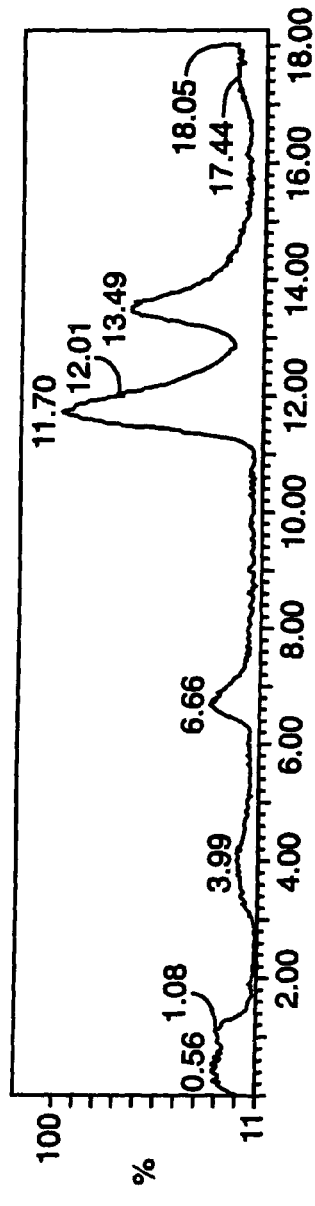
FIG. 4A
FIG. 4B
FIG. 4C

CAPILLARY LOOP WITH A BUILT-IN RETAINING FRIT

CROSS REFERENCE TO RELATED APPLICATIONS

This application claims benefit of and is a continuation of International Application No. PCT/US04/02967, filed Feb. 3, 2004 and designating the United States, which claims benefit of a priority to U.S. Provisional Application No. 60/444,749, filed Feb. 4, 2003. The content of which is expressly incorporated herein by reference in its entirety.

FIELD OF THE INVENTION

This invention relates generally to chromatographic columns, and in particular to columns having one or more retaining devices disposed therein.

BACKGROUND OF THE INVENTION

A common method used to separate analytes within a sample is liquid chromatography. Liquid chromatography employs specific chromatographic columns and one or more mobile phases which are used to both equilibrate the column and elute analytes therefrom. Chromatography columns are used to effectuate the separation, purification and study of analytes contained within a homogeneous or heterogeneous sample. Columns are packed with sorbent material (also referred to as the "stationary phase") that provides a chemical milieu with which analytes of a sample can interact. Generally, the sorbent material contains a functional group having a specific chemistry. For example, reverse-phase columns have a stationary phase comprising molecules with one or more hydrophobic groups. These hydrophobic groups, e.g., a $C_{18}$ hydrocarbon chain, will interact with other molecules via hydrophobic interaction. This hydrophobic interaction can be interrupted using an organic mobile phase, thus eluting various analytes from the stationary phase.

The most commonly used chromatographic columns, referred to herein as "conventional columns", are comprised of a column tube into which sorbent is packed, and inlet and outlet end fittings, which facilitate connection to the fluid stream, and which also contain filters that are designed to keep the sorbent bed within the column tube itself. These filters are disposed at each end face of the column tube.

Liquid chromatography columns can range in size depending upon the desirable application including small capillary columns. Capillary columns are particularly advantageous when relatively small sample sizes (referring to concentration) are examined. Another advantage observed with the use of capillary columns is their small connections to other columns or instruments thereby effectuating minimum loss of sample and gaining greater efficiency of chromatographic separation.

To effectuate concentrating a sample, retaining frits have been developed for chromatographic use. To date, however, most retaining frits are in a cartridge type format. Since their small dimensions make them difficult to use with relatively large dead volumes that lead to undesirable peak dispersion.

Thus, it is desirable to have retaining frits for capillary use that have a relatively large inner diameter in order to maximize the surface area of the stationary phase while at the same time their fluidic connections are smaller than their diameter. Moreover, it is desirable to have a retaining frit disposed within a capillary column thereby minimizing fluid transfer dynamics and effectuating separation efficiency.

SUMMARY OF THE INVENTION

The present invention pertains to both apparatus and methods for effecting increased chromatographic efficiency in a capillary column by employing a retaining frit disposed therein. By disposing a retaining frit within an analytic capillary column the void volume is significantly minimized. The columns and methods described herein produce a simplified analytical capillary and retaining frit apparatus that provides greater chromatographic efficiency. Additionally, the column of the instant invention maintains chromatographic fidelity by reducing the transfer diameter as well as facilitating fluidic connections in situ.

The capillary column of the present invention comprises a retaining capillary frit within an analytical capillary column. In this embodiment, the analytical capillary column which is comprised of stationary material has an inner diameter ranging from about 75 to about 150 µm and receives a retaining capillary frit having an inner diameter ranging from about 20 µm to about 10 µm. In one aspect of this embodiment, a glue-like polymeric substance like poly(dimethylsiloxane) is disposed between the inner surface of the analytical capillary column's surface and the outer surface of the retaining capillary frit This glue-like substance serves as a sealant.

In one embodiment of this invention, a single retaining frit is disposed within an analytical capillary column. In one aspect of this embodiment the retaining capillary frit is disposed within the analytical capillary column's inlet. In an alternative aspect of this embodiment, the retaining frit is disposed within the analytical capillary's outlet.

In another embodiment of the instant invention, an analytical capillary column comprises multiple retaining frits. In one aspect of this embodiment, a first retaining frit is disposed within the analytical column's inlet while a second retaining frit is disposed within the analytical column's outlet. A still further aspect of this embodiment embraces multiple retaining frits that are disposed adjacent to the analytical column's inlet.

In one embodiment, the invention pertains to a method of chromatographically separating two or more analytes within a sample by employing an analytical column comprising one or more retaining frits. In this embodiment, a sample comprising one or more analytes is introduced into a chromatographic system. This system comprises an analytical capillary column with one or more retaining frits disposed therein. In this embodiment, the retaining frit is generally continuous with the analytical column. The luminal areas of the retaining frit and analytical column align so as to facilitate movement of analyte from the retaining frit to the analytical column, or visa versa. In one aspect, the retaining frit and stationary phase of the analytical column are commonly housed within a single capillary. In this embodiment, the sample is admixed within a mobile phase that traverses within and through the two elements, i.e., the retaining element and the analytical element of the chromatographic column.

In a further embodiment, the present invention pertains to methods of manufacturing a chromatography capillary column comprised of an analytical element and one or more retaining elements. In one aspect of this embodiment, a retaining capillary frit is threaded into an analytical capillary. The retaining frit necessarily possesses a narrower diameter than said analytical capillary. The retaining frit is secured into position within the analytical capillary. The retaining frit is held in to position using a polymeric glue-like substance such as PDMS. This polymeric glue-like substance is disposed between the outer surface of the retaining frit and the inner surface of the analytical capillary in the region where the retaining frit is disposed within the analytical capillary. The inner retaining frit can be disposed within the analytical capillary adjacent to the region of the stationary phase. This stationary phase can be any commercially available stationary phase or one that is specifically manufactured.

DESCRIPTION OF THE DRAWINGS

FIG. 4 depicts chromatograms using a trapping column with a retaining frit of the present invention:

DETAILED DESCRIPTION

The present invention pertains to both apparatus and methods for effecting increased chromatographic efficiency in a capillary column by employing one or more retaining frits. The retaining frit is disposed within an analytical capillary column. By disposing the retaining frit within the analytical capillary column thereby forming a continuous column, several advantages result therefrom, for example, the void volume is significantly minimized thus promoting greater chromatography efficiency. The columns and methods described herein produce a simplified analytical and retaining frit apparatus that provide greater chromatographic efficiency. Additionally, the column of the instant invention maintains chromatographic fidelity by reducing the transfer diameter as well as facilitating fluidic connections in situ.

The present invention pertains to an analytical column having two identifiable elements. One such element is the retaining frit. This retaining frit is a capillary that is disposed within or adjacent to an analytical element. The analytical element is the portion of the capillary column that comprises a stationary phase.

Figure 1:
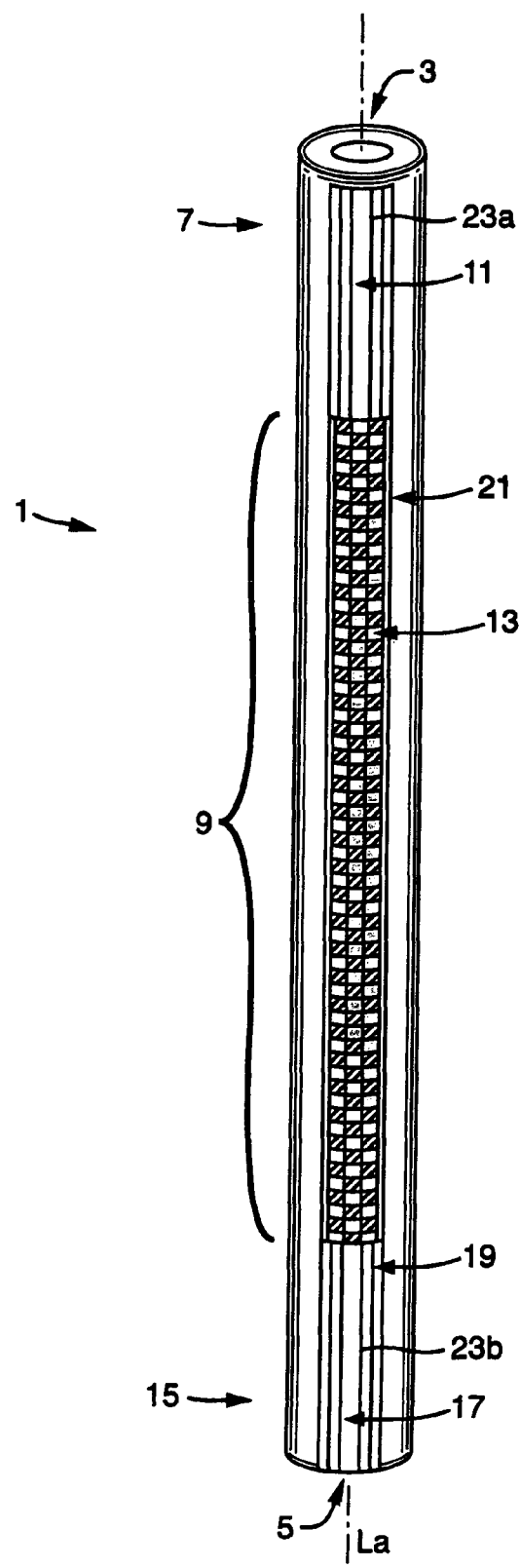
FIG. 1 depicts one embodiment of this invention where there are two retaining frits within one capillary column.

FIG. 1 depicts one embodiment of the present invention. In this figure, the inlet 3 and outlet 5 are arbitrarily positioned top and bottom, this positioning is merely for convenience of the reader. However, both the inlet 3 and outlet 5 are typical chromatographic elements such that each can make fluidic connections to other elements of the chromatographic system. In operation, a sample containing one or more analytes enters the capillary column 1 at the inlet 3. In this embodiment, the inlet 3 comprises a first retaining frit (or element) 7. The inner diameter for the frit can range from about 10 µm to about 20 µm; whereas the outer diameter can range from about 90 µm to about 150 µm. In one aspect the luminal dimensions of this first retaining frit 7 is 20 µm by 90 µm. The luminal dimensions can vary depending upon the column but is less than the analytical element 9. The length of the frit along the longitudinal axis (La) can range from about 0.5 cm to about 25 cm. The sample passing through the luminal space 11 of the first retaining element 7 and then traverses into the analytical element 9 which contains the stationary phase 13.

The luminal dimensions of the analytical element 9 can be range from about 100 µm to about 150 µm for the inner diameter, and from about 360 µm to about 720 µm for the out diameter. For example, the dimensions of the analytical element can be 100 µm by 360 µm. The dimensions of the longitudinal axis (La) of the analytical element 9 can range from about 1 cm to 20 cm is the typical range, but longer beds can be prepared. The stationary phase of the analytical element 9 can be comprised of any commercially available stationary phase, alternatively, it can be comprised of a stationary phase specifically manufactured for a particular purpose. Nevertheless, it is here in the analytical element 9 (specifically the stationary phase 13) that the analytes contained within the sample undergo specific interaction with the chemical groups of the stationary phase 13.

In the embodiment depicted by FIG. 1 the sample exiting the analytical element 9 enters a second retaining element 15 that is disposed at the outlet position 5 of the capillary column 1. As was the case for the first retaining element 7, the luminal dimensions 17 of the second retaining element 15 are smaller than that of the analytical element 9. The retaining element's luminal dimensions of the first and/or second retaining element 7, 15 can range from about inner diameters from 10 µm to 50 µm. Typically, however these dimensions are smaller than the luminal dimensions of the analytical element 9. Analytes of the sample egress the second retaining element 15 via outlet 5. The analytes could now conceivably enter an instrument for further processing or detection that is in fluidic connection with the capillary column 1. Examples of such instruments include, but are not limited to, mass spectrometers, binding analysis instruments, NMR instruments, and detectors like ultraviolet light or fluorescent detectors.

In the present embodiment, the retaining elements 7, 15 are disposed adjacent to the analytical element 9 in such a manner such that their respective lumens align in order to form a continuous luminal region. In this aspect, there is no loss of fidelity due to the apposition of retaining element 7, 15 with the analytical element 9 such that luminal areas 111 and 17 align with luminal area 13. There are several advantages attendant to such arrangement, for example, there are no void volumes that are formed between the retaining element(s) 7, 15 and the analytical element 9 as they are within a continuous structure. As a result, more efficient chromatographic separation can be performed as compared to conventional columns. This design eliminates the need for sintering to prepare a frit, hence the end of the capillary column is no longer very fragile, i.e., the column design is rugged and easier to use.

The retaining element or elements (as in the case of FIG. 1) are disposed securely within capillary surface 21. Disposed between the outer surface 23a, 23b of the inlet and outlet retaining elements 7 and 15, respectively, and the inner surface of the analytical column's capillary 21 is a polymeric substance that acts like a glue. This glue-like substance seals the outer surface 23a, 23b of the retaining element with the inner surface of the analytical column's capillary 21. See FIG. 1. An example of an appropriate glue-like substance that can be employed in the present invention is poly(dimethylsiloxane) or "PDMS". Other glue-like polymeric substances that can be used to seal a retaining element to an analytical capillary column include, but are not limited to, epoxies, resins, and adhesives.

During the manufacturing process, one or more retaining elements are disposed within an analytical column. A glue-like substance like PDMS is disposed between the two capillaries (i.e., the retaining capillary and the analytical capillary), specifically, between the outer surface of the retaining element capillary and the inner surface of the analytical capillary. Heat can then be applied in order to effectuate fusion of the two capillaries. Temperatures ranging from about room temperature (~25° C.) to about 110° C. can be applied. The arrangement of the retaining capillary disposed within the analytical capillary provides for a low thermal mass. Column heating is facilitated allowing for temperature assisted retaining and maintaining a constant temperature throughout a separation. For example, we typically trap proteins at low temperatures and then elute them at elevated temperatures. The manufacture of the individual capillaries (both retaining and analytical) can be performed by methods known to those skilled in the art.

The capillary column 1 of the present invention can range in length from about 3 cm to 25 cm. Further, depending upon the length of the capillary column, the retaining element can range in length from about 0.5 cm to about 25 cm. Moreover, the analytical element can range in length from about 1 cm to about 20 cm.

The capillary elements can be composed of any substance typically used to create capillary columns. These substances include, but are not limited to, fused silica, stainless steel, or polymeric compositions. In one embodiment, a composition is used which retains some flexibility, but sufficient strength to act as a chromatography column. In another embodiment, the second and third capillaries are non-reactive or inert to the sample, stationary phase and mobile phase.

In one embodiment of the present invention, multiple retaining elements are adjacently disposed along or within an analytical capillary. These retaining elements are designed such that they can be removed easily from the overall capillary column apparatus. For example, a retaining element could be snapped-off from the remaining column apparatus. In this way if a retaining element becomes occluded with material it can be simply removed from the column apparatus. The luminal dimensions of the retaining elements are less than that of the analytical element that contains the stationary phase. The junction between adjacent retaining elements is such that the material, such as fused silica, can be comfortably snapped or separated by means well known in the art (such as filing the material) without compromising the fluidic connection with the rest of the chromatographic system and fluidic connection between the retaining elements with one another or with the analytical element. In this embodiment, these multiple retaining elements can be employed to preserve the analytical column by collecting contaminants contained within a sample matrix.

Figure 2:
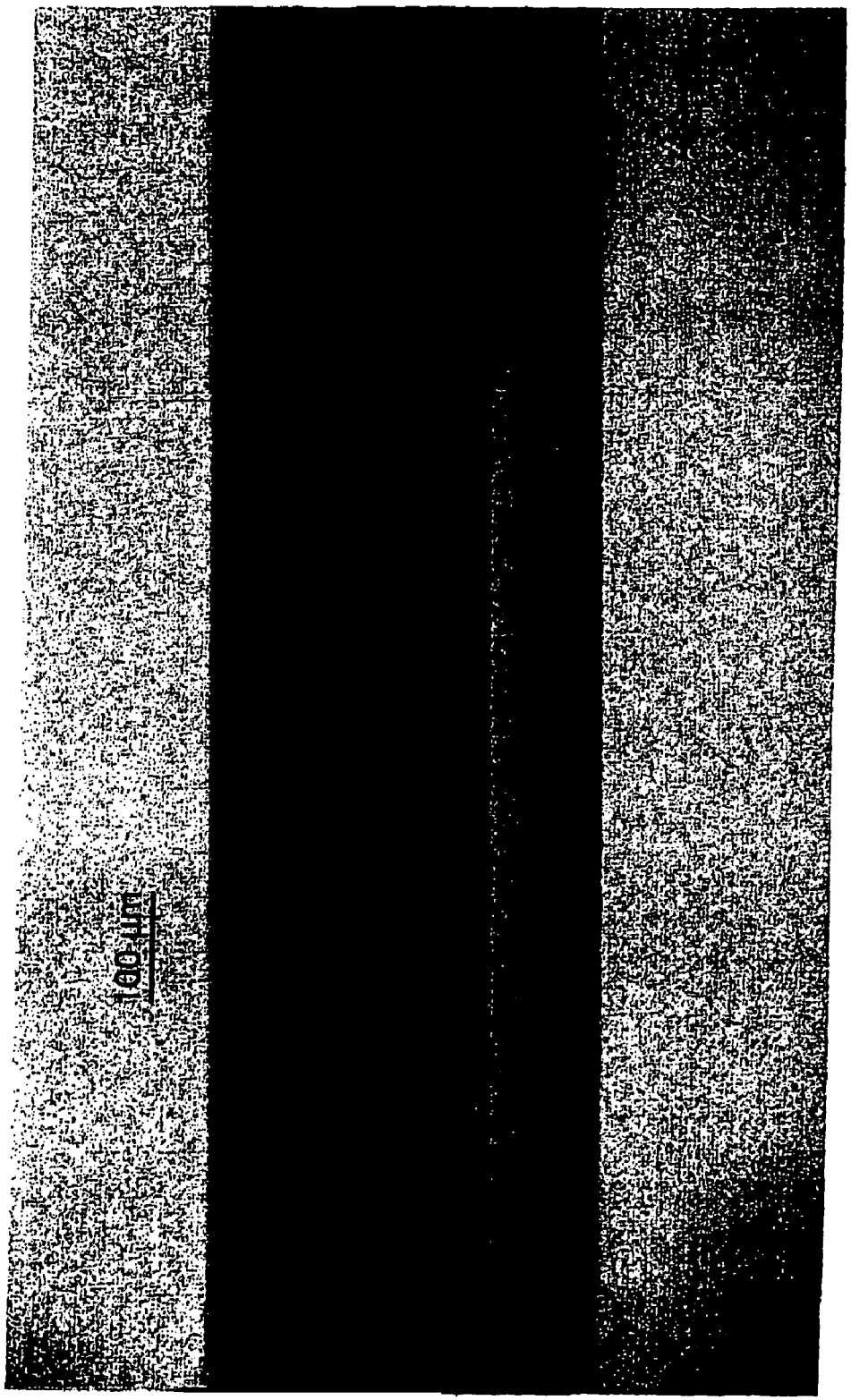
FIG. 2 is a digital image of a retaining frit adjacent to a stationary phase element of a capillary chromatography column.

A further embodiment of this invention pertains to a process of chromatographically separating a sample containing analytes employing a capillary column comprising one or more retaining elements. In this embodiment, the capillary column can have one or more retaining elements as depicted in FIG. 1. A sample of analytes is introduced under appropriate conditions into the capillary column using a mobile phase that is under pressure. This mobile phase carries the analytes into and through the capillary column. Returning to FIG. 1, the sample enters the capillary column 1 via the inlet 3. Disposed within the inlet position 3 is a first retaining element 7. The analytes in the sample enter the retaining element 7 and are concentrated there before entering the analytical element 9 where the stationary phase 13 resides. (The juncture between the retaining and analytical elements can be seen in FIG. 2.) As mentioned above, there can be multiple retaining elements aligned proximate to the inlet. This could be the case if these columns were, for example, guard columns. Nevertheless, the analytes enter the stationary phase 13 where they undergo differential adsorption. Depending upon the capillary column employed, the analytes that egress from the analytical column can enter another retaining element (such as that depicted in FIG. 1), enter another analytical instrument, such as a detector, or exit the chromatographic system, perhaps by entering a collection or waste vessel.

The following examples are intended to illustrate an embodiment of the present invention and should not be viewed as limiting the scope of the instant invention in any manner.

EXAMPLES

Example 1

Figure 3A:
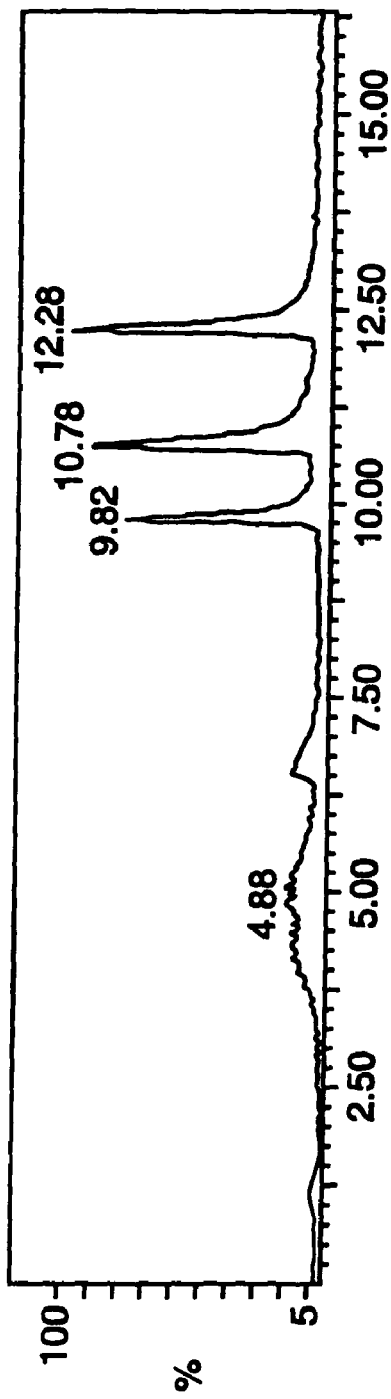
FIG. 3 depicts chromatograms illustrating the effect of conventional trapping column.
Figure 3B:
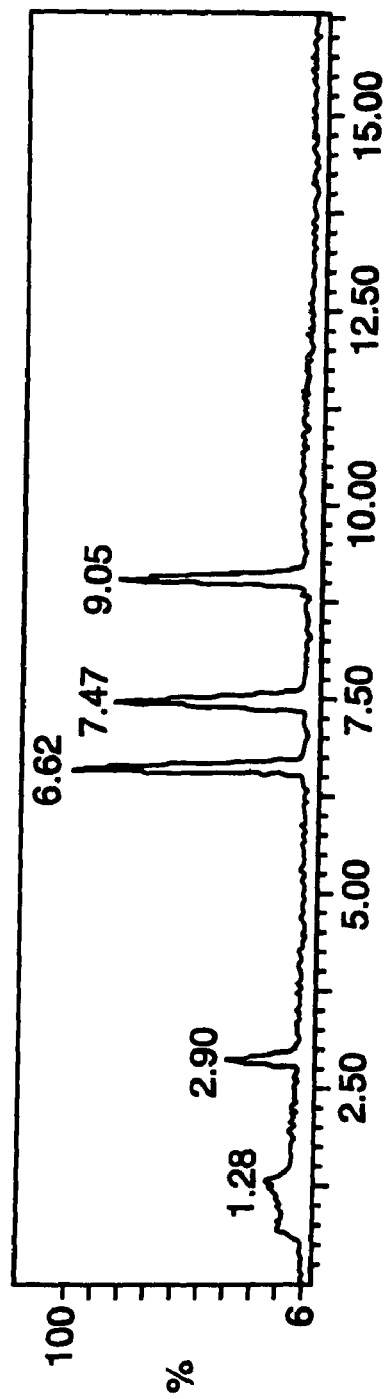

The impact of the design of commercially available trapping columns on chromatographic separations is illustrated in FIG. 3. Chromatogram A in FIG. 3 shows a separation of Sigma Peptide Standard H2016 (comprised of Gly-Tyr, Val-Tyr-Val, methionie enkephalin, leucine enkephalin, and angiotensin II) after retaining with a standard retaining frit. Gradient elution of the peptide mixture was accomplished using 5-35% B (0.1% formic acid in acetonitrile) over 30 minutes. Mobile phase A consisted of a 2:98 mixture of acetonitrile and water (0.1% formic acid). Detection was via a Micromass Q-Tof2 mass spectrometer. It is noted that the peaks are broad and tail a great deal. Once the trapping column is removed, the chromatographic peak shape dramatically improves and is as expected (as depicted in FIG. 3B).

Example 2

FIG. 4B illustrates the performance of the present invention operating as a trapping column (bed length 20 mm Waters 5.0 µm Symmetry™ C18) in comparison to no trapping column (FIG. 4A) and a commercially available Waters 350 µm×5 mm (Symmetry C18, 5 µm) Opti-pak™ trapping column (FIG. 4C) using the Sigma Peptide Standard. Gradient elution of the peptide mixture was accomplished using 5-35% B (0.1% formic acid in acetonitrile) over 30 minutes. Mobile phase A consisted of a 2:98 mixture of acetonitrile and water (0.1% formic acid). Detection was via a Micromass Q-Tof2 mass spectrometer. It is readily apparent that chromatographic peak shape suffers considerable when the Opti-pak™ column is used in contrast to the superior peak shape achieved with the invention.

Example 3

Figure 5A:
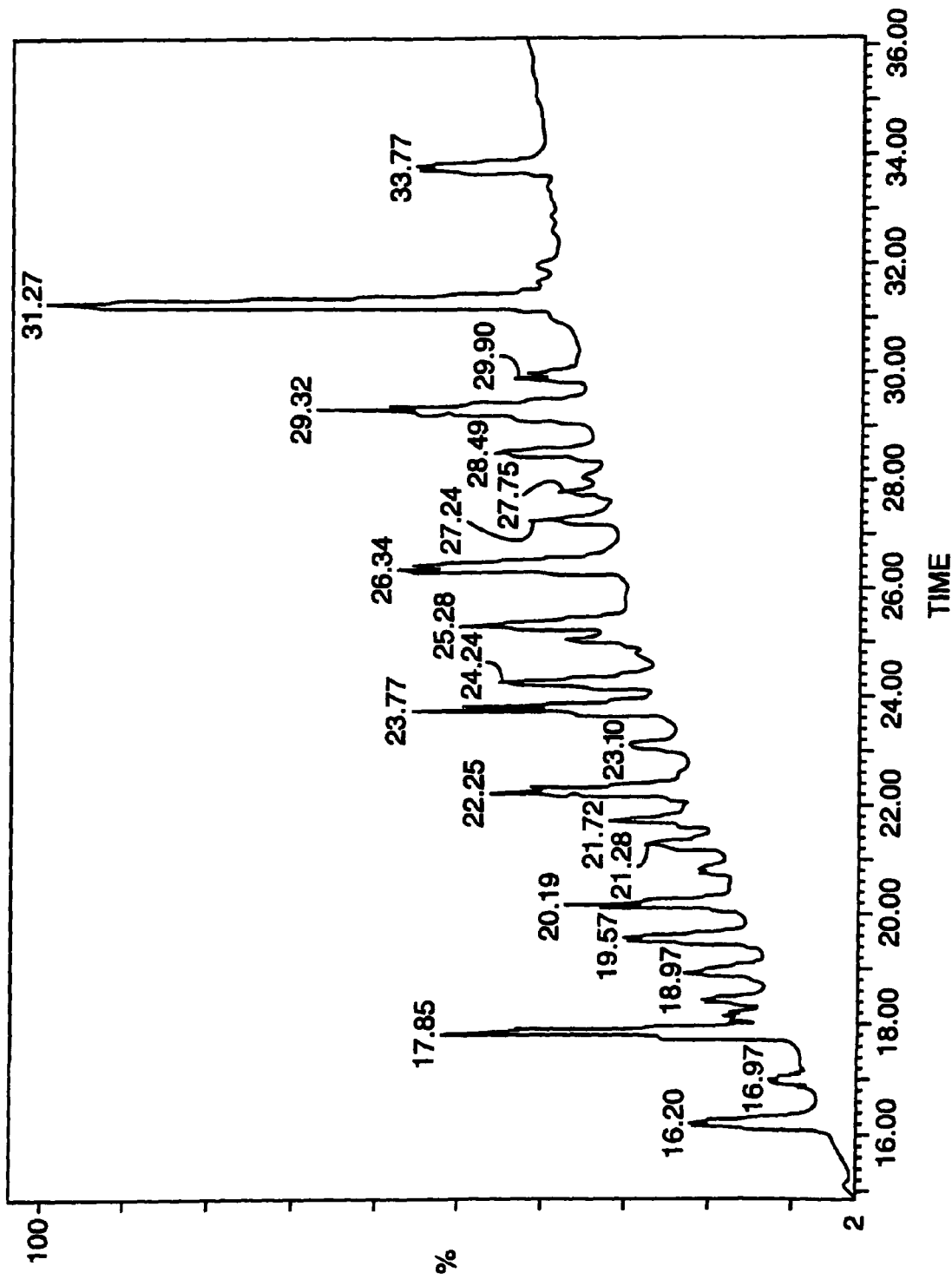
FIG. 5 depicts chromatograms employing a trapping and analytical column with retaining frits of the present invention.
Figure 5B:
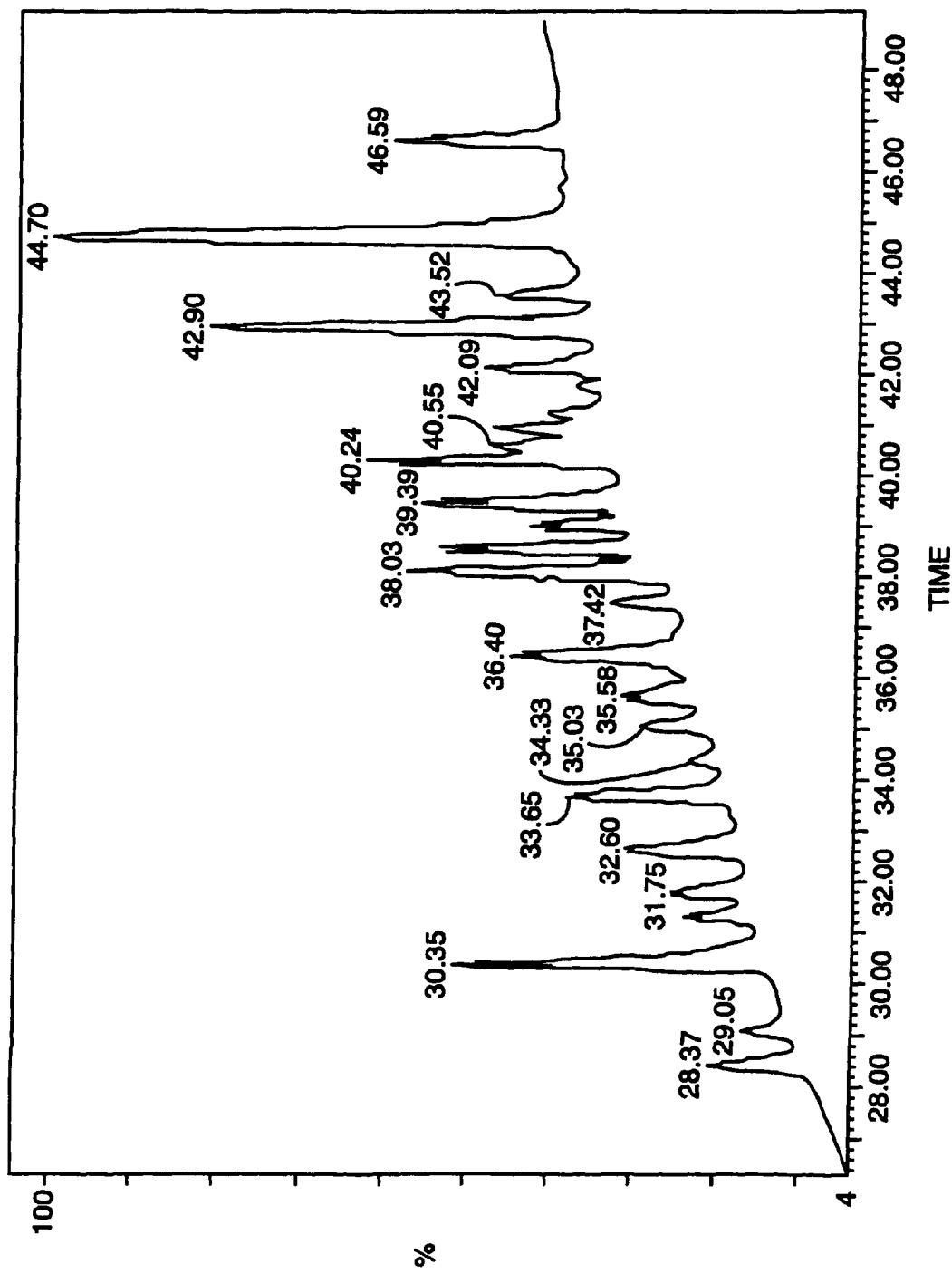
Figure 6:
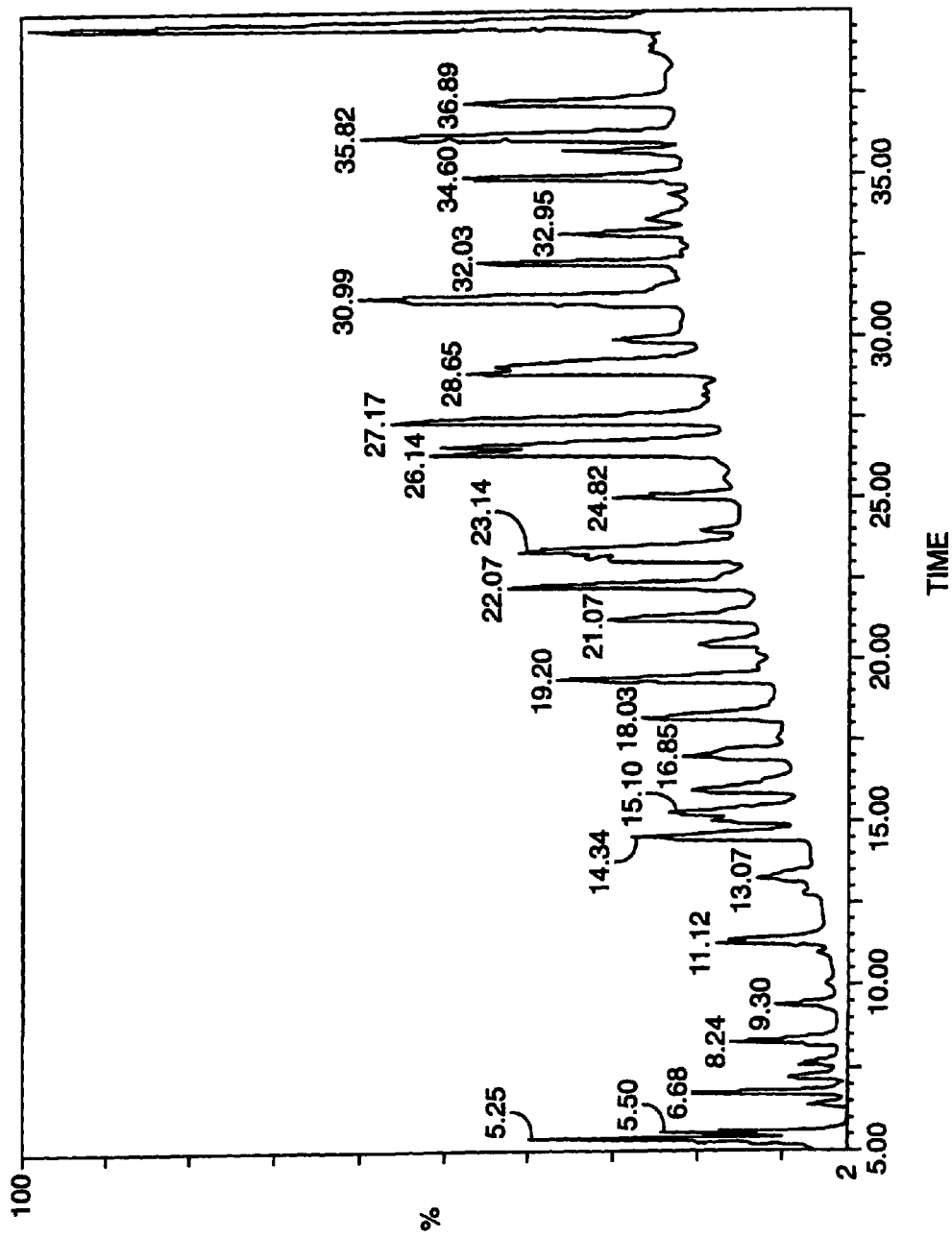
FIG. 6 depicts a chromatogram using an analytical column with retaining frit of the present invention.

In evaluating the performance of the invention, two assessments were made. FIG. 5A displays a typical chromatogram for enolase digest with direct elution through an in-line trapping column and analytical column without performing a retaining experiment. For this experimental protocol, a retaining phase 20 mm in length and comprised of Waters 5.0 µm Symmetry™ C18 was employed with an analytical phase 100 mm in length comprised of Waters 3.5 µm Symmetry C18. Gradient elution of the enolase digest was carried out using a programmed gradient consisting of 3-55% B (0.1% trifluoroacetic acid in acetonitrile) in 30 minutes. Eluent A consists of 0.1% trifluoroacetic acid in water. Detection was Ultraviolet at 210 nm. From this chromatogram, one observes excellent peak shape and chromatographic resolution. In a typical retaining experiment, the digest is loaded onto the retaining frit off-line, and subsequently eluted from the retaining frit onto the analytical column. FIG. 5B is the chromatographic result for the aforementioned experiment. A nominal loss of resolution is observed.

Example 4

A performance evaluation of the analytical nanocolumn format of the invention with a bed length of 10 cm and consisting of Waters 3.5 µm Symmetry C18 as the stationary phase was made using an enolase digest. Gradient elution of the enolase digest was carried out using a programmed gradient consisting of 3-55% B (0.1% trifluoroacetic acid in acetonitrile) in 30 minutes. Eluent A consists of 0.1% trifluoroacetic acid in water. Detection was Ultraviolet at 210 nm. Excellent chromatographic resolution and peak shape are achieved with the invention. Peak widths are comparable to those applications.

Of course, one skilled in the art will appreciate further features and advantages of the invention based on the above-described embodiments.

Accordingly, the invention is not to be limited by what has been particularly shown and described, except as indicated by the appended claims.

What is claimed is:

1. A device for separating compounds held in solution comprising:
   a first tube having a cylindrical wall having an inner surface defining a chamber having a first diameter, an exterior surface defining a second diameter, a first end and a second end, said first end for discharging a fluid and said second end for receiving a fluid, said chamber having at least one media section for containing a solid phase media and at least one frit section for receiving a frit element;
   a first media contained within said at least one media section;
   at least one frit element comprised of a second tube having a cylindrical wall having an inner surface having a third diameter, an exterior surface defining a fourth diameter, a third end and a fourth end, said fourth diameter smaller than said second diameter and said second tube disposed and fixed within said first tube within one frit section with said frit element between said exterior surface and said interior surface at one of said third end and fourth end abutting against said media to retain said media in said chamber, said media separating compounds held in solution as said solution flows through said chamber of said first tube.

2. The device of claim 1 wherein said at least one frit element has one end selected from said third end and said fourth end aligned with one end of said first tube, said one end selected from the group consisting of said first end and said second end, to provide minimal dead space associated with bandspreading.

3. The device of claim 1 wherein said fourth diameter is smaller than said first diameter.

4. The device of claim 1 wherein said fourth diameter is between approximately 90 and 150 µm.

5. The device of claim 1 wherein said first diameter is between approximately 100 and 150 µm.

6. The device of claim 1 wherein said second tube has a length that is between approximately 0.5 and 25 cm.

7. The device of claim 1 wherein said first tube has a length that is between approximately 1.0 and 20 cm.

8. The device of claim 1 comprising at least a first frit element and a second frit element and at least two frit sections, said first frit element positioned within a first frit section at said first end of said first tube and said second frit element positioned within a second frit section at said second end of said first tube.

9. The device of claim 1 wherein said one or more frit elements are secured in said first tube with a glue.

10. The device of claim 9 wherein said one or more frit elements are secured by an adhesive.

11. The device of claim 10 wherein said one or more frit elements are secured by a polydimethelseloxane (PDMS) elastomer.

12. The device of claim 1 wherein said first tube has at least one intermediate frit region interposed between a first media section and a second media section for receiving a frit element, and said device further comprises a frit element received and fixed in said intermediate frit region to retain media, said intermediate frit region defining at least one cleavage point to allow a spent media section to be cleaved from an unspent media section to allow said unspent media section to continue to receive solutions and separating compounds.

13. The device of claim 1 wherein said first tube and second tube are capillaries.

14. The device of claim 13 wherein said capillaries are comprised of fused silica.

* * * * *